United States Patent
Janssen et al.

(10) Patent No.: US 8,842,283 B2
(45) Date of Patent: Sep. 23, 2014

(54) APPARATUS, SYSTEM, AND METHOD FOR DETECTING ENGINE FLUID CONSTITUENTS

(75) Inventors: John M. Janssen, Henrico, VA (US); Frederick H. Lindner, Aesch (CH); Jacob Y. Wong, Goleta, CA (US)

(73) Assignee: Cummins Inc., Columbus, IN (US)

( * ) Notice: Subject to any disclaimer, the term of this patent is extended or adjusted under 35 U.S.C. 154(b) by 0 days.

(21) Appl. No.: 13/540,551

(22) Filed: Jul. 2, 2012

(65) Prior Publication Data

US 2012/0325184 A1     Dec. 27, 2012

Related U.S. Application Data

(63) Continuation of application No. 13/017,771, filed on Jan. 31, 2011, now Pat. No. 8,218,147.

(51) Int. Cl.
    *G01N 21/00*     (2006.01)
    *G01N 21/85*     (2006.01)

(52) U.S. Cl.
    CPC ............................. *G01N 21/85* (2013.01)
    USPC ........................................ 356/438; 356/432

(58) Field of Classification Search
    USPC ........... 356/432–442, 70, 128–136, 335–343, 356/73; 359/586–589; 60/276
    See application file for complete search history.

(56) References Cited

U.S. PATENT DOCUMENTS

| | | | |
|---|---|---|---|
| 4,578,762 A * | 3/1986 | Wong | ............................. 702/32 |
| 4,694,173 A | 9/1987 | Wong | |
| 4,756,622 A | 7/1988 | Wong | |
| 4,795,240 A | 1/1989 | Wong et al. | |
| 4,850,697 A | 7/1989 | Schoennauer et al. | |
| 4,924,095 A | 5/1990 | Swanson, Jr. | |
| 5,241,367 A | 8/1993 | Grob et al. | |
| 5,464,982 A | 11/1995 | Drucker et al. | |
| 5,464,983 A | 11/1995 | Wang | |
| 5,583,339 A | 12/1996 | Black et al. | |
| 5,617,720 A | 4/1997 | Achleitner et al. | |
| 5,748,311 A * | 5/1998 | Hamann et al. | ............... 356/336 |
| 5,767,776 A | 6/1998 | Wong | |
| 5,798,700 A | 8/1998 | Wong | |
| 5,834,777 A | 11/1998 | Wong | |
| 5,889,199 A | 3/1999 | Wong et al. | |
| 5,894,373 A | 4/1999 | Wong | |
| 5,945,924 A | 8/1999 | Marman et al. | |
| 5,966,077 A | 10/1999 | Wong | |
| 6,029,442 A | 2/2000 | Caren et al. | |
| 6,047,543 A | 4/2000 | Caren et al. | |
| 6,048,500 A | 4/2000 | Caren et al. | |
| 6,107,925 A | 8/2000 | Wong | |
| 6,166,647 A | 12/2000 | Wong | |
| 6,237,575 B1 | 5/2001 | Lampert et al. | |

(Continued)

*Primary Examiner* — Tri T Ton
(74) *Attorney, Agent, or Firm* — Krieg DeVault LLP

(57) ABSTRACT

A system for detecting engine fluid constituents includes an engine having a sample channel having a conduit for a working engine fluid. The system includes an electromagnetic (EM) source that emits EM radiation through a first metal tube, where the EM radiation is EM energy at a wavelength of interest. The system further includes an EM detector that receives a remainder radiation through a second metal tube, the remainder radiation including the remaining EM radiation after passing through the sample channel. The system includes a controller that determines a composition indicator signal representative of an amount of a constituent in the working engine fluid in response to a strength of the remainder radiation, and determines a concentration of a component of interest according to the composition indicator signal.

34 Claims, 9 Drawing Sheets

(56) References Cited

U.S. PATENT DOCUMENTS

| | | |
|---|---|---|
| 6,253,544 B1 | 7/2001 | Miller et al. |
| 6,264,899 B1 | 7/2001 | Caren et al. |
| 6,321,531 B1 | 11/2001 | Caren et al. |
| 6,330,794 B1 | 12/2001 | Caren et al. |
| 6,344,798 B1 | 2/2002 | Schell |
| 6,357,223 B1 | 3/2002 | Caren et al. |
| 6,810,660 B2 | 11/2004 | Hepburn et al. |
| 6,810,718 B2 | 11/2004 | Wilson et al. |
| 6,842,243 B2 | 1/2005 | Tokhtuev et al. |
| 6,917,038 B2 | 7/2005 | Zheng et al. |
| 6,982,431 B2 | 1/2006 | Modlin et al. |
| 7,007,547 B2 | 3/2006 | Philipp et al. |
| 7,084,963 B2 | 8/2006 | Leipertz |
| 7,176,460 B1 | 2/2007 | Wong |
| 7,178,331 B2 | 2/2007 | Blakeman et al. |
| 7,186,979 B1 | 3/2007 | Wong |
| 7,202,948 B2 | 4/2007 | Buckley et al. |
| 7,214,939 B1 | 5/2007 | Wong |
| 7,240,482 B2 | 7/2007 | Hepburn |
| 7,264,785 B2 | 9/2007 | Blakeman et al. |
| 7,313,911 B2 | 1/2008 | Pfeifer et al. |
| 7,409,823 B2 | 8/2008 | Price et al. |
| 7,480,044 B2 | 1/2009 | Leiperz |
| 8,218,147 B2 * | 7/2012 | Janssen et al. ............... 356/438 |
| 8,223,337 B2 | 7/2012 | Janssen et al. |
| 2002/0154289 A1 * | 10/2002 | Wilks, Jr. ............... 356/70 |
| 2004/0237505 A1 | 12/2004 | Leipertz |
| 2005/0076655 A1 | 4/2005 | Wong |
| 2005/0247066 A1 | 11/2005 | Myhre |
| 2006/0251548 A1 | 11/2006 | Willey et al. |
| 2006/0256330 A1 | 11/2006 | Leipertz |
| 2007/0029487 A1 | 2/2007 | Wong et al. |
| 2007/0029488 A1 | 2/2007 | Wong |
| 2007/0068495 A1 | 3/2007 | Karst |
| 2008/0295494 A1 | 12/2008 | Driscoll et al. |
| 2008/0295499 A1 | 12/2008 | Driscoll et al. |
| 2009/0193794 A1 | 8/2009 | Robel et al. |
| 2010/0083636 A1 | 4/2010 | Wang et al. |
| 2010/0101213 A1 | 4/2010 | Tuomivaara et al. |

* cited by examiner

APPARATUS, SYSTEM, AND METHOD FOR DETECTING ENGINE FLUID CONSTITUENTS

CROSS REFERENCE TO RELATED APPLICATIONS

The present application is a continuation of U.S. patent application Ser. No. 13/017,771 filed on Jan. 31, 2011 now U.S. Pat. No. 8,218,147 which claims the benefit of U.S. patent application Ser. No. 12/818, 837 filed on Jun. 18, 2010 which claims the benefit of U.S. patent application Ser. No. 12/610,818 filed on Nov. 2, 2009, which claims the benefit of U.S. Provisional Patent Application No. 61/197,897 filed Oct. 31, 2008, which are hereby incorporated by reference in their entirety for all purposes.

BACKGROUND

The technical field relates generally to detection of constituent concentrations in engine fluids. Reliably monitoring the combustion process inside an internal combustion engine presents several challenges. Frequently, engine environments operate at very high temperatures that preclude use of many standard sensor types. Further, engine combustion constituents typically include soot and unburned hydrocarbons that can hamper operation of various sensing technologies. Thus, there is an ongoing demand for further contributions in this area.

SUMMARY

One embodiment of the present application is a unique optical sensing technique. Other embodiments including unique devices, apparatus, systems, and methods to remove debris that accumulates on an optical sensing window in an adverse environment. Further embodiments, forms, objects, features, advantages, aspects, and benefits shall become apparent from the following description and drawings.

DESCRIPTION OF THE ILLUSTRATIVE EMBODIMENTS

Figure 1:
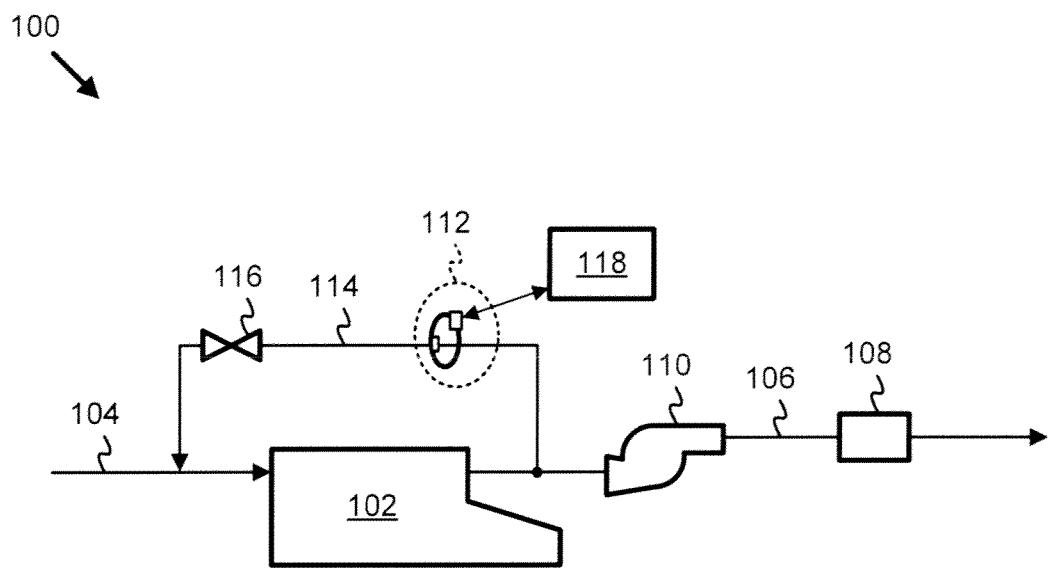
FIG. 1 is a schematic diagram of a system for detecting engine fluid constituents.

For the purposes of promoting an understanding of the principles of the invention, reference will now be made to the embodiments illustrated in the drawings and specific language will be used to describe the same. It will nevertheless be understood that no limitation of the scope of the invention is thereby intended, any alterations and further modifications in the illustrated embodiments, and any further applications of the principles of the invention as illustrated therein as would normally occur to one skilled in the art to which the invention relates are contemplated and protected.

FIG. 1 is a schematic diagram of a system 100 for detecting engine fluid constituents. In certain embodiments, the system 100 includes an engine 102 having a sample channel (refer to FIG. 2) comprising a conduit 114 for a working engine fluid. The conduit 114 in the illustration of FIG. 1 is an EGR recirculation path, and the engine fluid in the illustration of FIG. 1 is recirculating exhaust gas flowing in the conduit 114. In certain embodiments, the conduit 114 may be any conduit having a working engine fluid therein, including, without limitation, an exhaust flow path 106, an engine intake path 104, a fuel line, a coolant line, a portion of an intake manifold, an intake port for an individual cylinder of a multi-cylinder engine, a portion of an exhaust manifold, and an exhaust port for an individual cylinder of the multi-cylinder engine. In certain embodiments, the working engine fluid includes engine exhaust gas, engine oil, engine coolant, recirculating exhaust gas, fuel, engine intake gas, and/or engine intake gas corresponding to a single cylinder of a multi-cylinder engine. In certain embodiments, the system further includes a device 112 for determining a concentration of a constituent of the engine fluid. Reference FIG. 2 for details of an exemplary embodiment of the device 112.

In certain embodiments, the system 100 further includes a controller 118. The controller 118 is structured to determine a concentration of a component of interest in the working engine fluid. The controller 118 includes communications to sensors and actuators throughout the system 100, and such communications may be through networks, datalinks, wireless communications, or other communication methods known in the art. The controller 118 may be a single device or distributed devices. In certain embodiments, the controller 118 includes a computer processor and computer readable memory of any known type. In certain embodiments, the controller 118 includes modules structured to functionally execute procedures performed by the controller. The use of the term modules emphasizes the implementation independence of the procedures. Modules may be elements of computer readable code, and may be grouped, divided, and/or distributed among various devices comprising the controller 118. Reference FIG. 3 for details of an exemplary embodiment of the controller 118.

In certain embodiments, the component of interest includes a nitrogen-oxygen compound, a hydrocarbon, a sulfur containing compound, ammonia, a compound representative of a natural gas content, a carbon-oxygen compound, and/or an amount of particulates. For example, the compound of interest in certain embodiments includes methane and ethane, and the controller 118 calculates a natural gas content in response to the amount of methane and ethane in the working engine fluid. In certain embodiments, the component of interest includes methane, ethane, and/or propane. In certain embodiments, the component includes nitrogen oxide ($N_yO_x$), nitric oxide (NO), nitrogen dioxide ($NO_2$), and/or nitrous oxide (N₂O). In certain embodiments, the component of interest includes carbonyl sulfide (O=C=S), carbon monoxide, and/or carbon dioxide.

In certain embodiments, the component of interest is component indicative of engine wear, and the controller 118 is further structured to determine an engine wear index in response to the concentration of the component of interest. For example, the compound of interest may be brass (indicative of wear in certain bearings), iron (indicative of wear in certain engine blocks), a material known to be in the piston rings, and/or any other compound that indicates engine wear in a specific application.

In certain embodiments, the component of interest includes a component indicative of fuel quality, and the controller 118 is further structured to determine a fuel quality index in response to the concentration of the component of interest. For example, the compound of interest may be nitrogen which in certain applications is indicative of a filler used in natural gas fuels. The concentration of nitrogen in the natural gas, in certain embodiments, can be indicative of the fuel quality. In another example, the compound of interest may correspond to an additive, tracer, aromatic compound, or other compound in the fuel that in specific applications may be indicative of a quality of the fuel.

In certain embodiments, the working engine fluid includes engine fuel or engine oil, and the component of interest includes sulfur or a sulfur compound. In certain embodiments, the amount of sulfur allowed in the engine fuel and/or engine oil may be regulated, and the controller 118 determines the concentration of sulfur in the fuel and/or oil to provide that information to an engine controller (not shown, but may be included in the controller 118) for appropriate response.

In certain embodiments, the working engine fluid includes engine oil, and the component of interest comprises one of water and ethylene glycol. In certain embodiments, the presence of coolant in engine oil may be indicative of certain types of failure, and the controller 118 determines the concentration of sulfur in the fuel and/or oil to provide that information to an engine controller (not shown, but may be included in the controller 118) for appropriate response.

In certain embodiments, the working engine fluid includes engine coolant, the component of interest includes a component indicative of engine coolant quality, and the controller 118 is further structured to determine an engine coolant quality index in response to the concentration of the component of interest. The engine coolant quality, for example, may be a description of the water/ethylene glycol ratio, and may be utilized by the engine controller (not shown, but may be included in the controller 118), for example in a warranty assessment after an engine failure.

In certain embodiments, the working engine fluid includes engine oil, the component of interest includes a component indicative of engine oil quality, and the controller is further structured to determine an engine oil quality index in response to the concentration of the component of interest. For example, the component of interest may track the present concentration of an additive in the oil to determine when the oil should be changed. In another example, the component of interest may include a compound or group of compounds from which an API number or other characteristic of the oil may be determined to evaluate the quality of the oil. In certain embodiments, the working engine fluid includes a engine oil, engine fuel, engine coolant, an exhaust gas fluid, a recirculating exhaust gas fluid, and/or an engine intake fluid.

Figure 2:
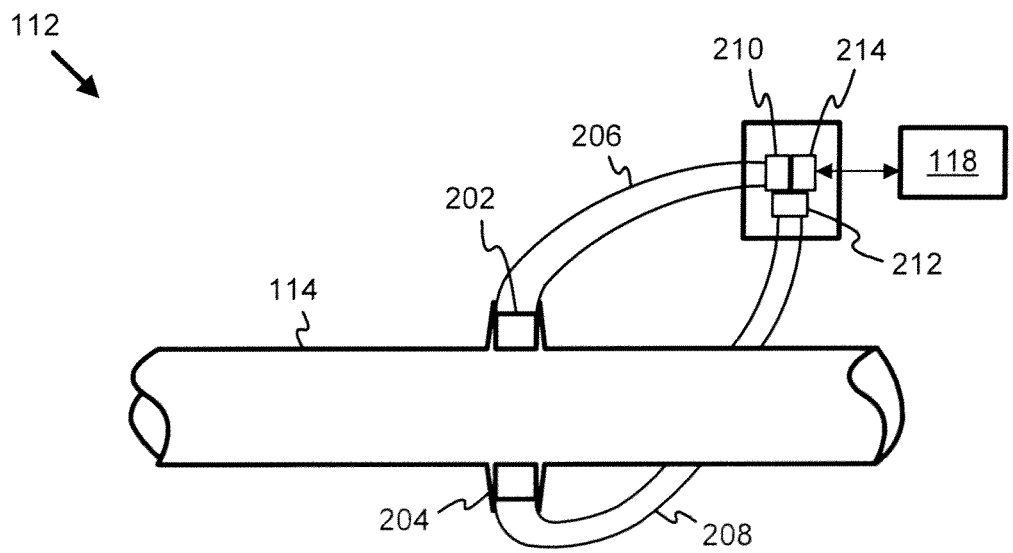
FIG. 2 is a schematic illustration of a device for detecting engine fluid constituents.

FIG. 2 is a schematic illustration of a device 112 for detecting engine fluid constituents. The device 112 includes an electromagnetic (EM) source 214 structured to emit EM radiation through a first metal tube 206. The EM radiation includes EM energy at a wavelength of interest. In certain embodiments, the EM energy may be provided by a broad spectrum EM source (e.g. an incandescent source) and passed through an interference filter 210 to remove frequencies outside the wavelength of interest. In certain embodiments, the interference filter 210 is a bandpass filter removing frequencies outside a desired range of frequencies. In certain embodiments, the EM source 214 is a laser that emits the EM radiation at a wavelength of interest and may not include an interference filter 210. In certain embodiments, the EM source 214 is a tunable laser that emits EM radiation at a number of frequencies of interest, for example to detect a number of components of interest. In certain embodiments, the EM source 214 includes a plurality of sources that each emit a different wavelength, or the EM source 214 may be a broad spectrum emitter (e.g. an incandescent source), and a plurality of interference filters 210 allow different wavelength ranges to the first metal tube 206 at different times to detect different components of interest.

In certain embodiments the EM source 214 includes at least one of a laser device, a light emitting diode, and a gallium arsenide light emitting diode. In certain embodiments, the device 112 includes the interference filter 210 disposed between the EM source 214 and the sample channel 114, with the interference filter 210 including a band pass filter. In certain embodiments, the first metal tube 206 and the second metal tube 208 each comprise extruded aluminum, extruded stainless steel, a polished metal, and/or a machined metal. The tubes 204, 206 should have sufficient resistance to temperature and corrosion in the system 100, and have sufficient internal reflectivity to convey the EM radiation to the sample channel 114 and back from the sample channel 114.

In certain embodiments, the device 112 further includes an EM detector 212 structured to receive a remainder radiation through a second metal tube 208, the remainder radiation including the remaining EM energy of the EM radiation after passing through the working engine fluid in the sample channel 114. In certain embodiments, the second metal tube 208 may be the same physical tube as the first metal tube 206, for example the EM radiation may pass through the first metal tube 206, reflect off a mirror opposing the entrance of the first metal tube 206, and pass back into the first metal tube 206, which is then acting as the second metal tube 208, back to the EM detector 212. In certain embodiments, the EM detector 212 includes a lead selenide detection device.

In certain embodiments, the device 112 includes a first window 202 isolating the first metal tube 206 from the sample channel 114 and the working engine fluid, and a second window 204 isolating the second metal tube 208 from the sample channel 114 and the working engine fluid. The window material should be selected to allow sufficient EM energy through the window 202, 204 at the wavelength of interest that the EM detector 212 can distinguish the concentration of the component of interest through the expected operational range for the component of interest, or the portion of the expected operational range that is of interest. For example, if the component of interest is oxygen in an internal combustion engine application, the expected range may be zero to twenty-one percent oxygen by mole, or a lower range if, for example, values above a certain percentage are not of interest in a particular application.

Factors that affect the final strength of the received EM radiation include the available power of the EM source 214, losses in the interference filter 210, tubing 206, 208, the strength of the extinction response of the component of interest at the selected wavelength, and the optical path length across the sample channel 114. The material of the window 202, 204 should further be a material that withstands the thermal and chemical environment of the conduit 114, and further that can suitably conduct heat to allow a cleaning event (e.g. reference FIGS. 3 and 9, and related descriptions) and withstand the cleaning temperature of the cleaning event. The selection of a specific window material is dependent upon the application and is a mechanical step for one of skill in the art based upon the disclosures herein. In certain embodiments, the first window 202 and the second window 204 comprise a material selected from the group consisting of sapphire, glass, and diamond. In one example, the component of interest is carbon dioxide, the working engine fluid includes combustion exhaust gases, the wavelength of interest is about 4.26µ, the sample channel 114 has an optical path length of about 35 mm, and the window 202, 204 material is sapphire.

In certain embodiments, the first window 202 and the second window 204 are the same physical window, for example where the first metal tube 206 and the second metal tube 208 are the same physical tube. In certain embodiments, the device 112 includes a reflective device (e.g. a mirror, not shown) opposing the first window 202, for example where the first metal tube 206 and the second metal tube 208 are the same physical tube.

In certain embodiments, the system further includes a kit (e.g. as a portion of the device 112) having the first metal tube 206, the second metal tube 208, the first window 202, the second window 204, and at least a portion of the sample channel 114. In certain embodiments, the kit further includes means for quick removal and replacement. For example, the kit may include wing nuts, levered clamps, seals, and/or other quick disconnect devices to allow ready removal of the kit and installation of a replacement kit. In certain embodiments, means for quick removal and replacement further includes positioning of the device 112 within a system at a location where access is readily available—for example positioning the device where the starter, turbocharger 110, fan, or other components in the application are not blocking access to the kit.

Figure 3:
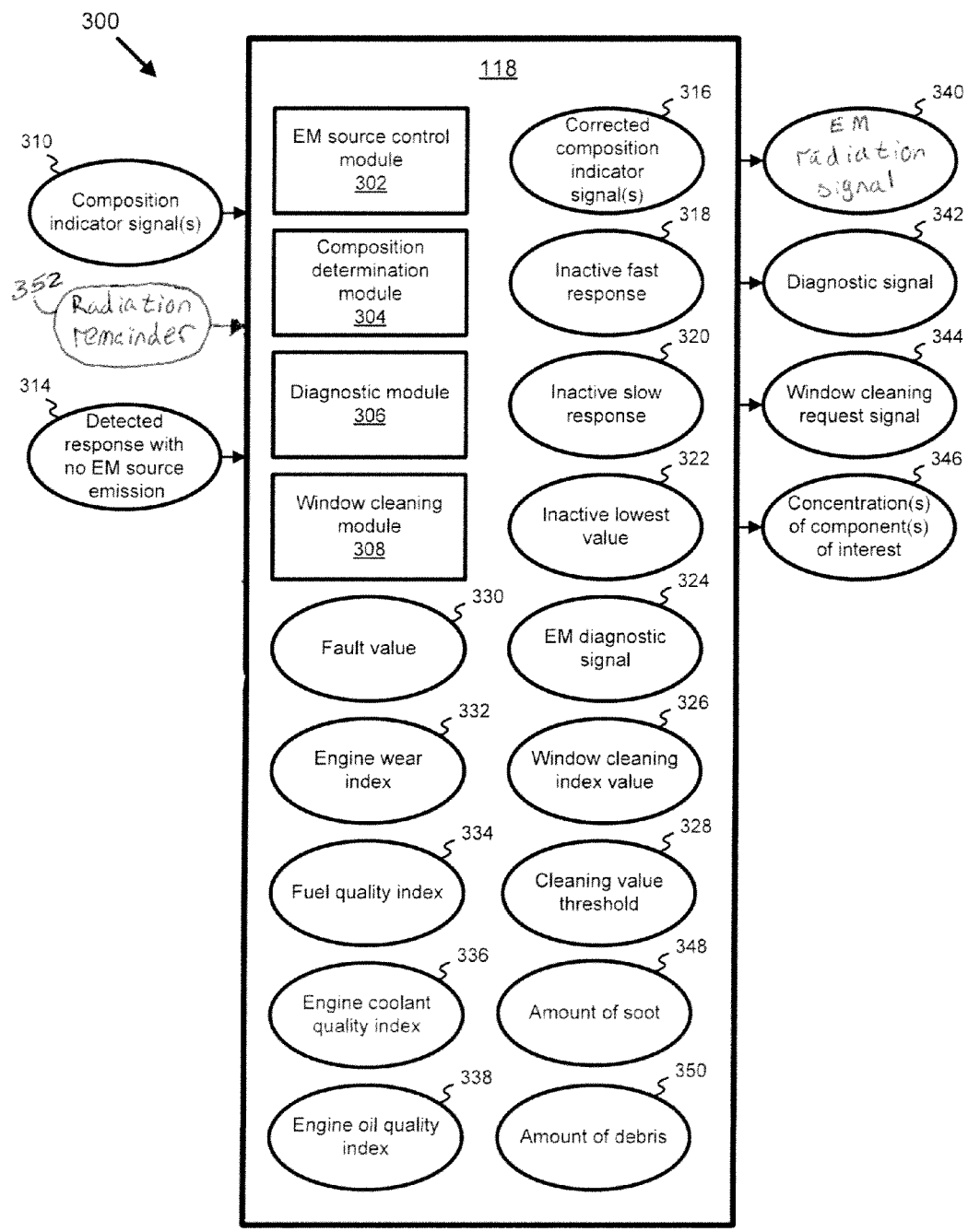
FIG. 3 is a schematic diagram of a controller structured to determine a concentration of a component of interest.

FIG. 3 is a schematic diagram of a controller 118 structured to determine a concentration of a component of interest. In certain embodiments, the controller 118 determines a composition indicator signal 310 in response to a strength of the remainder radiation 352, wherein the composition indicator signal 310 is representative of an amount of the compound of interest present in the sample channel 114. The controller 118 further determines a concentration of a component of interest 346 according to the composition indicator signal 310. For example, an EM detector 212 receives the EM remainder radiation 352, the controller 118 determines the composition indicator signal 310 based on the strength of the remainder radiation 352, and determines the concentration of a component of interest 346 according to the composition indicator signal 310.

In certain embodiments, a controller 118 includes an electromagnetic (EM) source control module 302 structured to provide an EM radiation signal 340. In certain embodiments, the EM source 214 emits EM radiation through the first metal tube 206 and the sample channel 114 in response to the EM radiation signal 340. In certain embodiments, the EM detector 212 receives the EM radiation from the sample channel 114 through a second metal tube 208, and provides the composition indicator signal 310 in response to a radiation remainder 352 strength at the wavelength of interest. In certain embodiments, the controller 118 includes a composition determination module 304 that determines the concentration of a component of interest 346 according to the composition indicator signal 310. For example, in certain embodiments, the composition indicator signal 310 may be an extinction value at the wavelength of interest, and the composition determination module 304 may utilize a lookup table that determines the concentration of a component of interest 346 as a function of the extinction value. The lookup table is calibrated according to the aspects of the system 100 that the device 112 is installed in, including the optical characteristics of the composition of interest, the relevant concentrations of the composition of interest, and the distance across the sample channel 114 that the EM radiation traverses.

In certain embodiments, the EM source control module 302 provides an EM diagnostic signal 324, and the EM source 214 emits an EM diagnostic radiation in response to the EM diagnostic signal 324. The EM diagnostic radiation includes energy at a diagnostic wavelength, and the EM detector 212 provides the radiation remainder 352 strength to the controller 118 while the EM diagnostic radiation is transmitted. The diagnostic module 306 provides a diagnostic signal 342 in response to the radiation remainder 352 strength at a diagnostic wavelength (or wavelengths). In certain embodiments, the EM diagnostic signal 324 is an instruction to perform a diagnostic test, and the diagnostic signal 342 is a qualitative or quantitative description of the results of the diagnostic test.

The diagnostic wavelength is a wavelength selected such that no expected components of the working engine fluid significantly absorb the diagnostic wavelength, except for "grey" or "black" components (i.e. components that absorb some fraction of all wavelengths roughly equivalently). In many circumstances, soot in the working engine fluid and debris deposited on the windows 202, 204 can be treated as grey matter with sufficient accuracy for many purposes.

In certain embodiments, the diagnostic module 306 determines an amount of soot 348 in response to the diagnostic signal 342. In certain embodiments, the amount of soot 348 is determined by attributing an entire loss between the EM radiation emitted by the EM source and the radiation remainder 352, or an entire loss between the radiation remainder 352 and a baseline diagnostic radiation remainder 352 strength, to absorption by soot in the working engine fluid. In certain embodiments, the diagnostic module 306 determines an amount of debris 350 deposited on the windows (202, 204), and accounts for EM radiation loss attributable to the amount of debris 350 when determining absorption by soot in the working engine fluid.

In certain embodiments, the composition determination module 304 determines the concentration of the component of interest 346 according a corrected composition indicator signal 316. In certain embodiments, the composition determination module 304 determines the corrected composition indicator signal 316 according to the equation:

$$CCIS = \frac{Active - Dark}{Inactive - Dark} \qquad \text{(Equation 1)}$$

In the example Equation 1, CCIS is the corrected composition indicator signal 316, Active is the composition indicator signal 310 before correction, Inactive is the diagnostic signal 342 or the radiation remainder 352 during a diagnostic test, and Dark is a detected response at a time when the EM source 214 is not emitting EM radiation, or a detected response with no EM source emission 314. For example, if the composition indicator signal 310 shows 70% (i.e. 30% absorption of the wavelength of interest), the diagnostic signal 342 shows 90% (i.e. the radiation remainder 352 is 90% during a previous diagnostic test), and the detected response with no EM source emission 314 is 2%, the composition indicator signal 310 is a value based on 70% while the corrected composition indicator signal 316 is a value based on ((70−2)/(90−2)) is 77%, or a little stronger than the directly indicated composition indicator signal 310 due to suppression of the composition indicator signal 310 by an amount of soot 348 and/or an amount of debris 350.

In certain embodiments, the diagnostic module 306 determines the amount of soot 348 by filtering the diagnostic signal 342 with a time constant less than 30 seconds to provide an Inactive fast response signal 318, filtering the diagnostic signal 342 with a time constant greater than 30 seconds to provide an Inactive slow response signal 320, and determining the amount of soot 348 according to the Inactive slow response signal 320 subtracted from the Inactive fast response signal 318. The 30-second value is exemplary only. The inactive fast response signal 318 is an indicator of total grey matter in the conduit 114 (i.e. soot plus debris) and the inactive slow response signal 320 is an indicator of long term grey matter in the conduit 114 (i.e. debris only). In certain embodiments, the inactive slow response 320 utilizes a relatively slow rising time constant and a relatively fast falling time constant, to bias the inactive slow response 320 to a lower value in the observed range of inactive values (i.e. of received diagnostic signal 312 values). In certain embodiments, diagnostic module determines an amount of debris 350 accumulated on the window(s) 202, 204 according to a lowest Inactive value 322 observed over time. For example, the diagnostic module 306 may track received diagnostic values 312, and reset the inactive lowest value 322 to the lowest observed value over a recent period—for example a lowest value observed in the last five minutes, or a lowest value observed during the most recent engine motoring event (i.e. when the engine was last not combusting any fuel).

In certain embodiments, the controller 118 further includes a window cleaning module 308 that provides a window cleaning index value 326 in response to the amount of debris 350 accumulated. In certain embodiments, the window cleaning module 308 is further structured to provide a window cleaning request signal 344 in response to the window cleaning index value 326 exceeding a cleaning threshold value 328. In certain embodiments, the system 100 includes a window cleaning means that cleans the window(s) in response to the window cleaning request signal 344.

In certain embodiments, the diagnostic module 306 determines a fault value 330, an engine wear index 332, a fuel quality index 334, an engine coolant quality index 336, and/or an engine oil quality index 338 in response to the concentration of the component of interest 346. In certain embodiments, the fault value 330 is an indication whether an engine 102 parameter is out of tolerance according to the concentration(s) of the component(s) of interest 346. In certain embodiments, the indices 332, 334, 336, 338 provide a value correlated to the underlying engine parameter—i.e. engine wear, fuel quality, engine coolant quality, and/or engine oil quality—according to the concentration(s) of the component(s) of interest 346.

Figure 4:
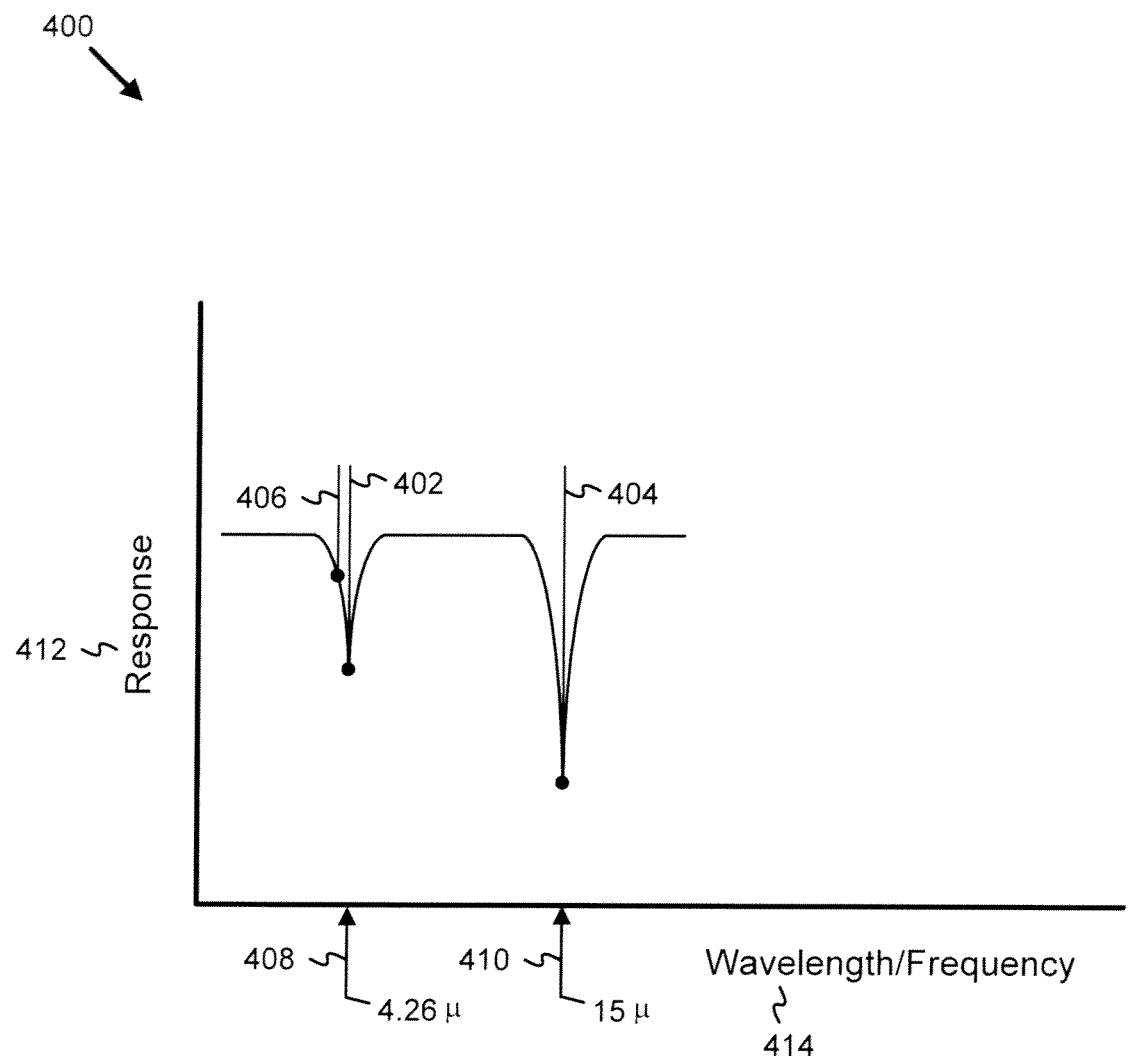
FIG. 4 is an illustration of a constituent wavelength response.

FIG. 4 is an illustration 400 of a constituent wavelength response. The illustration 400 includes a response value 412 versus a wavelength (or possibly frequency) value 414 for a component of interest. The constituent wavelength response illustrated in FIG. 4 is consistent with a simplified illustration for carbon dioxide, showing a first responsive wavelength 408 and a second, stronger, responsive wavelength 410. Depending upon the parameters of the system 100 (refer to the section referencing FIG. 2), a wavelength of interest for the EM radiation from the EM source 214 may be selected at either responsive wavelength 402, 404. In certain embodiments, the sample channel 114 may be too long, or the constituent concentrations expected may be too high, such that instead of using the stronger response wavelength 410, the weaker response wavelength 408 may be selected.

In certain embodiments, the wavelength of interest may be selected as one of the responsive wavelengths, for example selecting wavelength 402 and/or 404. In certain embodiments, the wavelength of interest may be selected as a wavelength near one of the responsive wavelengths, for example selecting wavelength 406. In certain embodiments, the wavelength of interest such that an extinction of the wavelength of interest is about 50% of an extinction of the responsive wavelength near the wavelength of interest (e.g. about what the wavelength of interest 406 indicates in FIG. 4). The extinction of the responsive wavelength may be measured as a peak value (e.g. a discrete value right on the responsive wavelength 408), or as an area under (or above) a range of wavelength values, such as a range of values allowed through the bandpass filter 210.

The selection of an off-nominal wavelength such as the wavelength of interest 406 allows for longer sample channel 114 lengths, higher constituent concentrations, and similar adjustments. The wavelength of interest may be variable or multiple in certain embodiments, for example providing higher extinction rates at lower constituent concentrations and lower extinction rates at higher constituent concentrations, or providing higher and lower extinction rates at all times and utilizing both extinction rates in calculating a composition indicator signal 310. In certain embodiments, the responsive wavelength includes a fundamental wavelength and/or a harmonic wavelength.

The schematic flow diagrams (FIGS. 5-9) and related descriptions which follow provide illustrative embodiments of operations related to the present application. Operations shown are understood to be illustrative only, and operations may be combined or divided, and added or removed, as well as re-ordered in whole or part, unless stated explicitly to the contrary herein.

Figure 5:
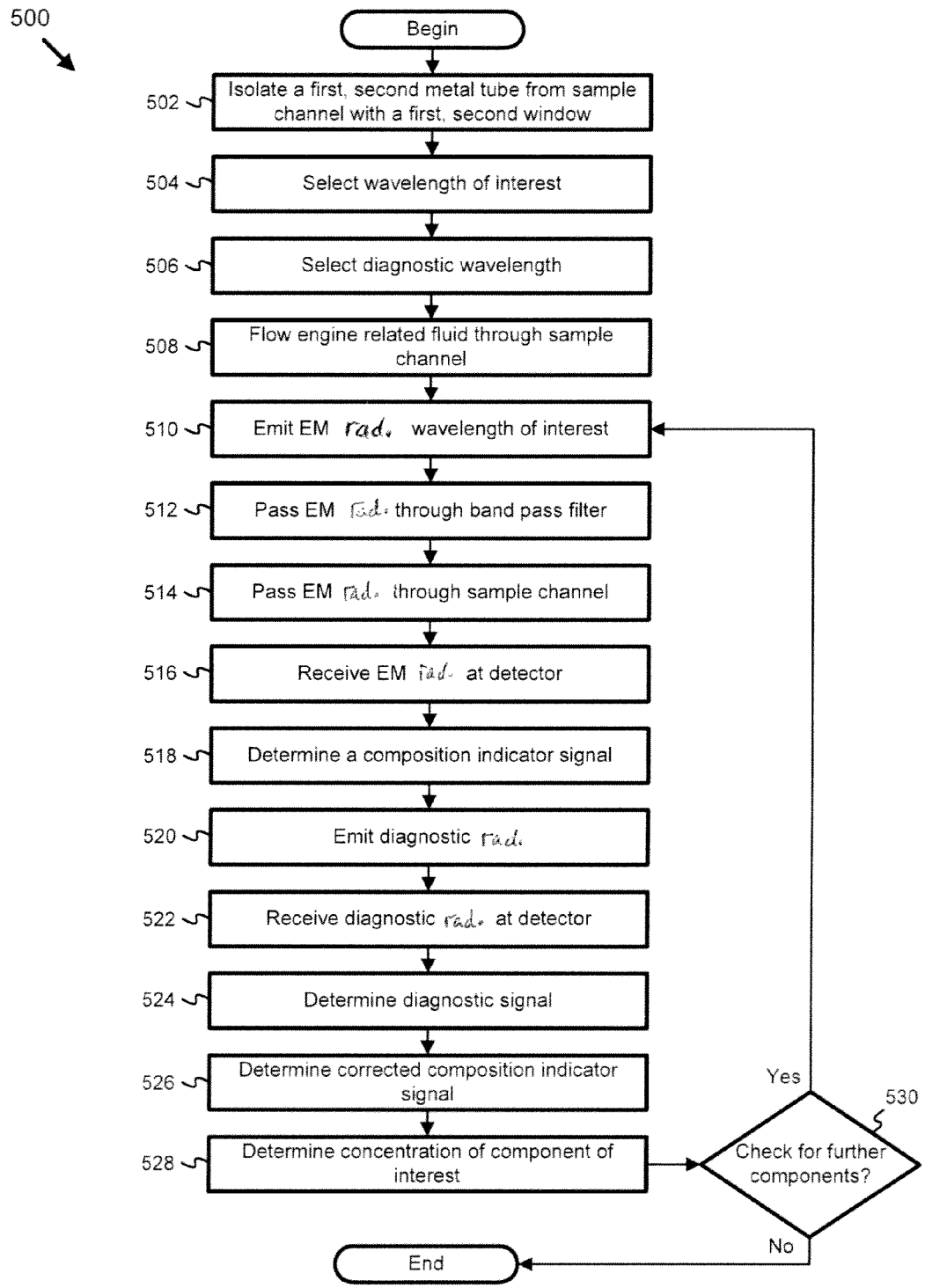
FIG. 5 is a schematic flow diagram of a procedure for determining a concentration of a component of interest.

FIG. 5 is a schematic flow diagram of a procedure 500 for determining a concentration of a component of interest. In certain embodiments, the procedure 500 includes an operation 502 to isolate the first metal tube (or other optical conduit) from the sample channel with a first window and isolating the second metal tube (or other optical conduit) from the sample channel with a second window. In certain embodiments, the procedure 500 further includes an operation 504 to select a wavelength of interest, and an operation 506 to select a diagnostic wavelength.

The procedure 500 includes an operation 508 to flow a working engine fluid through a sample channel, and an operation 510 to emit electromagnetic (EM) radiation comprising energy at a wavelength of interest through a first metal tube. The procedure 500 further includes an operation 512 to pass the EM radiation through a bandpass filter. The procedure 500 further includes an operation 514 to pass the EM radiation through the sample channel and an operation 516 to receive the radiation at an EM detector through a second metal tube. The procedure 500 further includes an operation 518 to determine a composition indicator signal in response to a remaining radiation strength at the wavelength of interest, where the composition indicator signal is representative of a concentration of a component of interest.

In certain embodiments, the procedure 500 includes an operation 520 to emit an EM diagnostic radiation including energy at a diagnostic wavelength, and an operation 522 to receive the remaining diagnostic radiation strength at the diagnostic wavelength at an EM detector. In certain embodiments, the procedure 500 further includes an operation 524 to determine a diagnostic signal in response to the remaining diagnostic radiation strength at the diagnostic wavelength. In certain embodiments, the procedure 500 further includes an operation 526 to determine a corrected composition indicator signal. The procedure further includes an operation 528 to determine a concentration of a component of interest according to the composition indicator signal by utilizing the corrected composition indicator signal. In certain embodiments, the procedure 500 further includes an operation 530 to check for whether concentrations should be determined for further components. In response to a determination that concentrations should be determined for further components, the procedure 500 includes operations 510-528 to emit EM radiation at a second (or third, fourth . . . etc.) wavelength of interest, and to determine a concentration of a second component of interest in response to the EM radiation at the second wavelength of interest.

Figure 6:
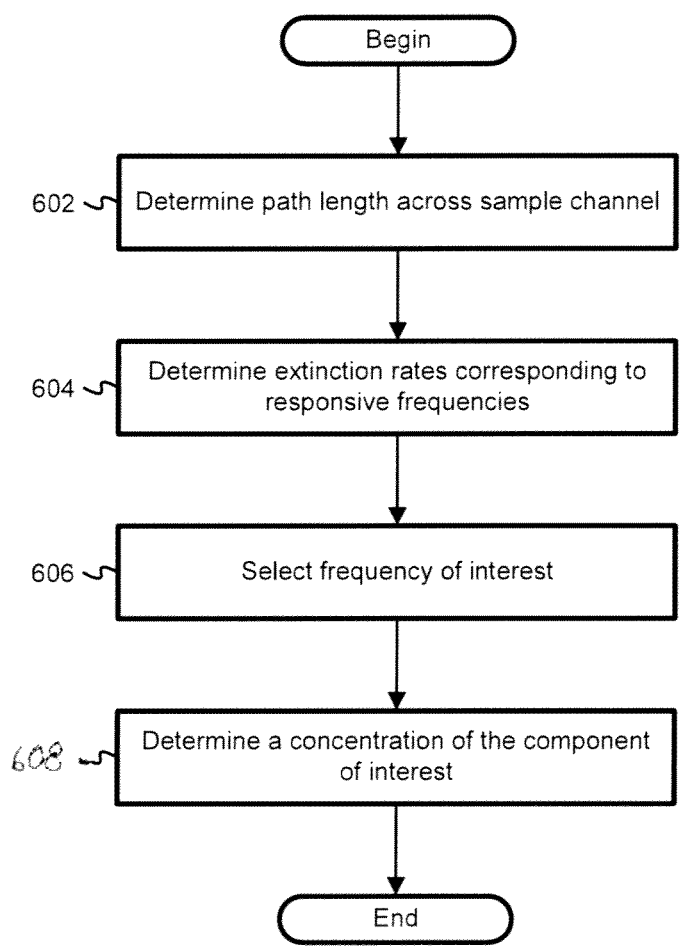
FIG. 6 is a schematic flow diagram of a procedure for designing an apparatus for determining a concentration of a component of interest.

FIG. 6 is a schematic flow diagram of a procedure 600 for designing an apparatus for determining a concentration of a component of interest. The procedure 600 includes an operation 602 to determine a path length across a sample channel, and an operation 604 to determine extinction rates corresponding to responsive wavelengths for a component of interest at a design range of concentration. The procedure 600 further includes an operation 606 to select a frequency of interest according to the extinction rates corresponding to the responsive frequencies for the component of interest at the design range of concentrations of the component of interest. In certain embodiments, the procedure 600 includes an operation 608 to determine a concentration of a component of interest, for example utilizing one or more operations from the procedure 500.

Figure 7:
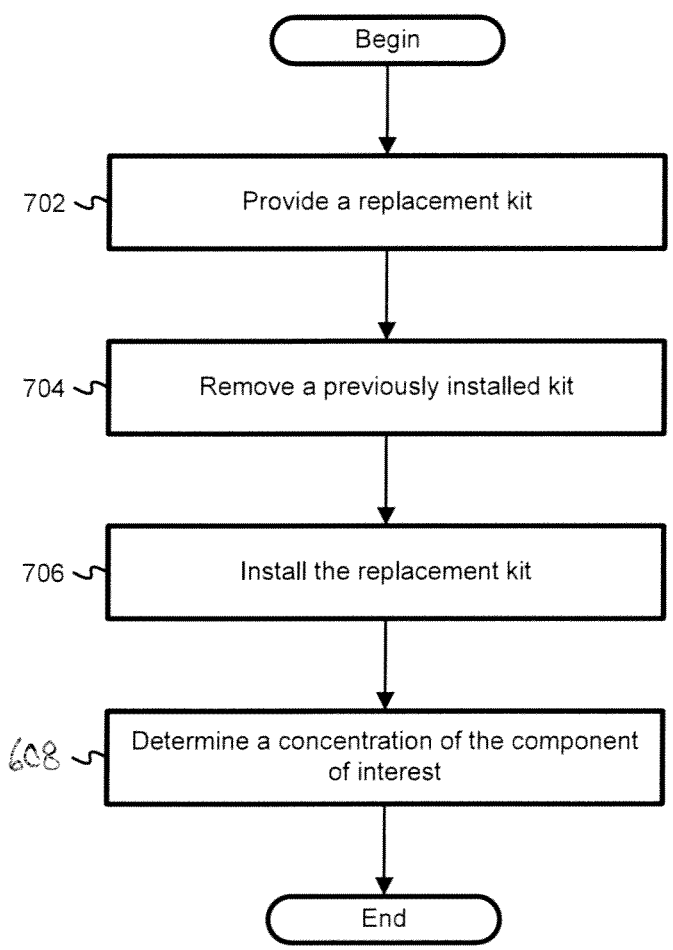
FIG. 7 is a schematic flow diagram of a procedure for replacing an apparatus for determining a concentration of a component of interest.

FIG. 7 is a schematic flow diagram of a procedure 700 for replacing an apparatus for determining a concentration of a component of interest. In certain embodiments, the procedure 700 includes providing a replacement kit comprising the first metal tube, the second metal tube, the first window, and the second window, and operations 704 including removing a previously installed kit from an engine. The procedure 700 further includes an operation 706 to install the replacement kit on the engine. In certain embodiments, the procedure 700 includes an operation 608 to determine a concentration of a component of interest, for example utilizing one or more operations from the procedure 500.

Figure 8:
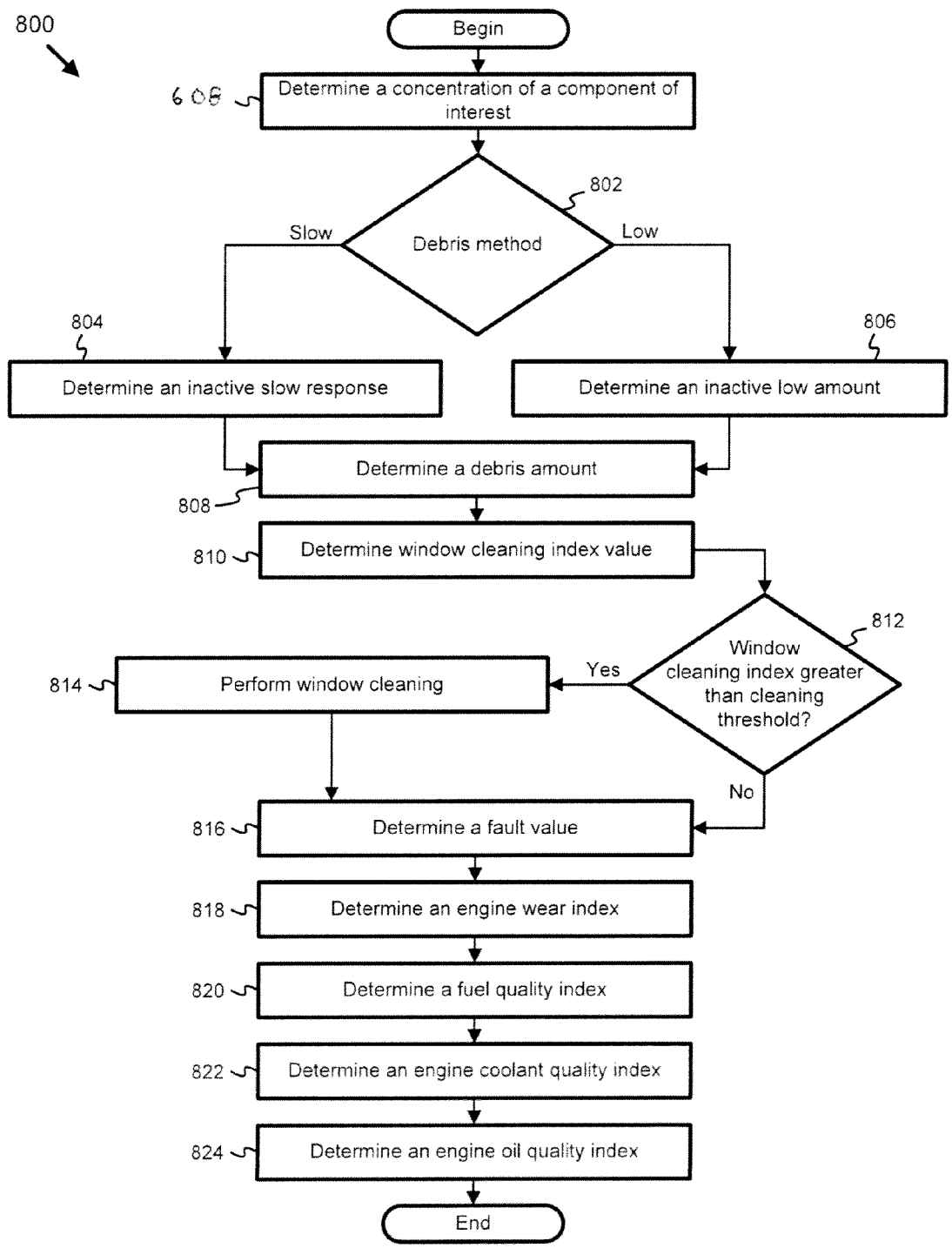
FIG. 8 is a schematic flow diagram of a procedure for determining a plurality of fluid indices.

FIG. 8 is a schematic flow diagram of a procedure 800 for determining a plurality of fluid indices. In certain embodiments, the procedure 800 includes an operation 608 to determine a concentration of a component of interest, for example utilizing one or more operations from the procedure 500. In certain embodiments, the procedure 800 further includes an operation 802 to determine whether a debris determination method includes an inactive slow response or an inactive low amount. In response to the procedure 800 including the inactive slow response, the procedure 800 includes an operation 804 to determine an inactive slow response, and an operation 808 to determine a debris amount in response to the inactive slow response. In response to the procedure 800 including an inactive low amount, the procedure 800 includes an operation 806 to determine an inactive low amount, and an operation 808 to determine a debris amount in response to the inactive low amount.

In certain embodiments, the procedure 800 includes an operation 810 to determine a window cleaning index value in response to the amount of debris accumulated. In certain embodiments, the procedure 800 further includes an operation 812 to determine whether the window cleaning index is greater than a cleaning threshold. In certain embodiments, the procedure 800 includes an operation 814 to perform a window cleaning event in response to determining the window cleaning index value exceeds a cleaning threshold value. In certain embodiments, the procedure includes an operation 816 to determine a fault value in response to the received diagnostic signal. In certain embodiments, the procedure 800 includes an operation 818 to determine an engine wear index 818, an operation 820 to determine a fuel quality index, an operation 822 to determine an engine coolant quality index, and/or an operation 824 to determine an engine oil quality index in response to the concentration(s) of the component(s) of interest.

Figure 9A:
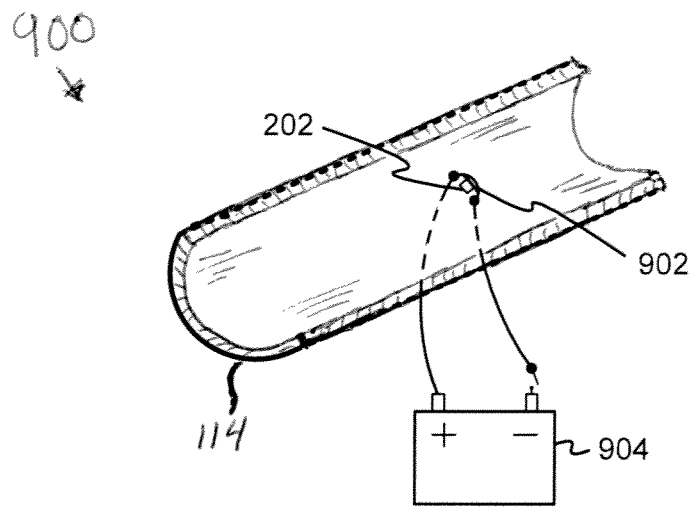
FIG. 9A is a schematic diagram of an apparatus for cleaning an optical element.

FIG. 9A is a schematic diagram of an apparatus for cleaning an optical element including a cutaway view of a sample channel 114. The apparatus 900 includes the optical element 202 and a means for cleaning the optical element. In certain embodiments, the apparatus 900 includes a wire 902 with a high thermal expansion coefficient, and the wire is positioned to sweep the optical element 202 upon a temperature increase event. In certain embodiments, the wire 902 may be a resistive wire that heats when a supply voltage 904 is applied, sweeping the wire 902 across the optical element 202.

Figure 9B:
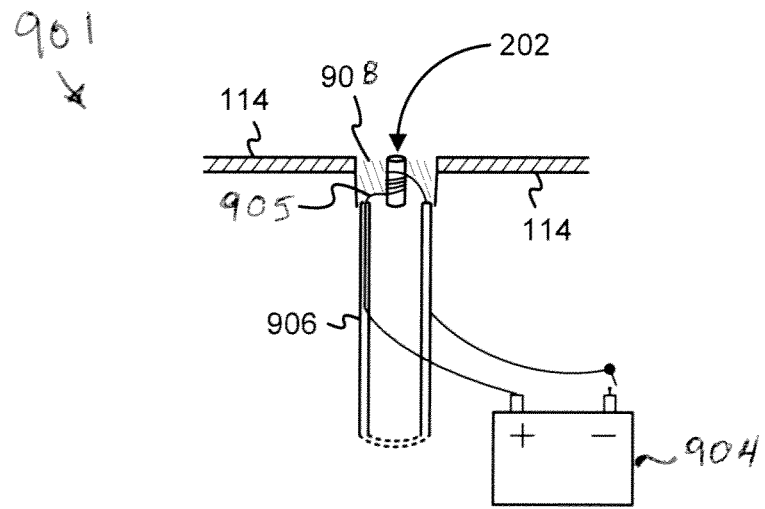
FIG. 9B is a schematic diagram of an apparatus for cleaning an optical element.

FIG. 9B is a schematic diagram of an apparatus for cleaning on optical element. The apparatus 901 includes the optical element 202, which may be a sapphire cylinder in certain embodiments, and a tube 906. In certain embodiments, a ceramic filler 908 or other heat resistant material provides a seal between the optical element 202 and the conduit 114. The apparatus 901 includes a means for cleaning the optical element 202 including a resistive wire 905 wrapped around a portion of the optical element 202, such that when the resistive wire 905 is heated the face of the optical element 202 exposed to the conduit 114 (i.e. the "window") is heated sufficiently to drive debris (through oxidation, evaporation, or other means) from the face of the optical element 202. A supply voltage 904 may be applied to the resistive wire 905 at times where a cleaning event is performed.

Figure 9C:
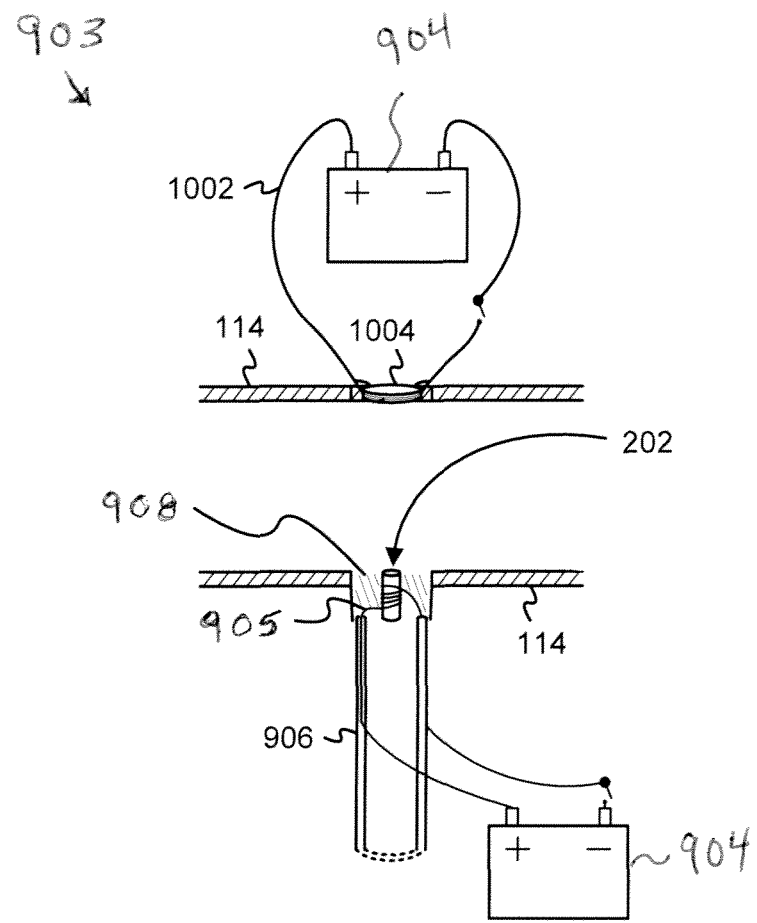
FIG. 9C is a schematic diagram of an apparatus for cleaning an optical element.

FIG. 9C is a schematic diagram of an apparatus 903 for cleaning an optical element. The apparatus 903 includes a resistive wire 1002 in thermal contact with a mirror 1004 positioned opposite an optical element 202. The resistive wire 1002 heats the mirror sufficiently to drive debris (through oxidation, evaporation, or other means) from the face of the mirror 204. A supply voltage 904 may be applied to the resistive wire 1002 at times where a cleaning event is performed.

As is evident from the figures and text presented above, a variety of embodiments according to the present invention are contemplated.

One exemplary embodiment is a method including interrogating a working engine fluid with electromagnetic (EM) radiation through a first conduit at a wavelength of interest. The method further includes detecting a response of the working engine fluid to the radiation through a second conduit, and generating a composition indicator signal representative of an amount of a constituent of the working engine fluid. In certain embodiments, the first conduit is a first metal tube and the second conduit is a second metal tube. In certain embodiments, the method further includes isolating the first metal tube from the sample channel with a first window and isolating the second metal tube from the sample channel with a second window.

In certain embodiments, emitting EM radiation comprises emitting EM radiation at the wavelength of interest from a laser. In certain embodiments, emitting EM radiation comprising energy at a wavelength of interest comprises emitting a broad EM radiation and passing the broad EM radiation through a band pass filter. In certain embodiments, the method further includes selecting the wavelength of interest as a wavelength near a responsive wavelength for the component of interest, but having reduced extinction relative to the responsive wavelength. In certain further embodiments, the method includes selecting the wavelength of interest such that an extinction of the wavelength of interest is about 50% of an extinction of the responsive wavelength.

In certain embodiments, the method further includes emitting EM radiation at a second wavelength of interest and determining a concentration of a second component of interest in response to the EM radiation at the second wavelength of interest.

In certain embodiments, the first metal tube and the second metal tube each comprise at least one metal selected from the metals consisting of extruded aluminum, extruded stainless steel, a polished metal, and a machined metal. In certain embodiments, the component of interest comprises carbon dioxide, and, wherein the first window and the second window comprise sapphire. In certain embodiments, the responsive wavelength includes one of a fundamental wavelength and a harmonic wavelength.

In certain embodiments, the method further includes determining a path length across a sample channel having the working fluid flowing therein, determining a plurality of extinction rates corresponding to a plurality of responsive frequencies for the component of interest at a design range of concentrations, and selecting a wavelength of interest according to the extinction rates corresponding to a plurality of responsive frequencies for the component of interest at a design range of concentrations of the component of interest. In certain embodiments, the method includes providing a replacement kit comprising the first metal tube, the second metal tube, the first window, and the second window, removing a previously installed kit from an engine, and installing the replacement kit on the engine.

In certain embodiments, the method further includes emitting an EM diagnostic radiation comprising energy at a diagnostic wavelength, and determining a received diagnostic signal in response to a remaining diagnostic radiation strength at the diagnostic wavelength. In certain embodiments, the method further includes emitting an EM diagnostic radiation including energy at a diagnostic wavelength, determining a received diagnostic signal in response to a remaining diagnostic radiation strength at the diagnostic wavelength, determining the concentration of the component of interest according to a corrected concentration indicator signal, and determining the corrected concentration indicator signal according to the equation:

$$CCIS = \frac{Active - Dark}{Inactive - Dark},$$

where CCIS is the corrected concentration indicator signal, Active is the concentration indicator signal, Inactive is the received diagnostic signal, and Dark is a detected response at a time when the EM source is not emitting a radiation.

In certain embodiments, the method includes tracking an Inactive fast response portion and an Inactive slow response portion, and determining an amount of soot in the working engine fluid by subtracting the Inactive slow response portion from the Inactive fast response portion. In certain embodiments, the method further includes isolating the first metal tube from the sample channel with a first window and isolating the second metal tube from the sample channel with a second window, determining an amount of debris accumulated on at least one of the first window and the second window, and wherein the determining an amount of debris accumulated comprises one of tracking an Inactive slow response portion and tracking a lowest Inactive observed over time. In certain embodiments, the method includes determining a window cleaning index value in response to the amount of debris accumulated. In certain embodiments, the method includes performing a window cleaning event in response to determining the window cleaning index value exceeds a cleaning threshold value. In certain embodiments, the method includes determining a fault value in response to the received diagnostic signal.

One exemplary embodiment is a system including an engine having a sample channel comprising a conduit for a working engine fluid, an electromagnetic (EM) source structured to emit EM radiation through a first metal tube, the EM radiation comprising EM energy at a wavelength of interest, an EM detector structured to receive a remainder radiation through a second metal tube, the remainder radiation comprising the remaining EM energy of the EM radiation after passing through the sample channel, and a controller. In certain embodiments, the controller is structured to determine a composition indicator signal in response to a strength of the remainder radiation and determine a concentration of a component of interest according to the composition indicator signal.

In certain embodiments the EM source includes at least one of a laser device, a light emitting diode, and a gallium arsenide light emitting diode. In certain embodiments, the EM detector includes a lead selenide detection device. In certain embodiments, the system includes an interference filter disposed between the EM source and the sample channel, the interference filter includes a band pass filter. In certain embodiments, the system includes a first window isolating the first metal tube from the sample channel, a second window isolating the second metal tube from the sample channel, and wherein the first window and the second window comprise a material selected from the group consisting of sapphire, glass, and diamond.

In certain embodiments, the working engine fluid comprises a fluid selected from the fluids consisting of engine exhaust gas, engine oil, engine coolant, recirculating exhaust gas, fuel, engine intake gas, and engine intake gas corresponding to a single cylinder of a multi-cylinder engine. In certain embodiments, the component of interest includes a nitrogen-oxygen compound, a hydrocarbon, a sulfur containing compound, ammonia, a compound representative of a natural gas content, a carbon-oxygen compound, and/or an amount of particulates. In certain embodiments, the component of interest includes methane, ethane, and/or propane. In certain embodiments, the component includes nitrogen oxide ($N_yO_x$), nitric oxide (NO), nitrogen dioxide ($NO_2$), and/or nitrous oxide ($N_2O$). In certain embodiments, the component of interest includes carbonyl sulfide (O=C=S), carbon monoxide, and/or carbon dioxide. In certain embodiments, the component of interest is component indicative of engine wear, and the controller is further structured to determine an engine wear index in response to the concentration of the component of interest. In certain embodiments, the component of interest includes a component indicative of fuel quality, and the controller is further structured to determine a fuel quality index in response to the concentration of the component of interest.

In certain embodiments, the working engine fluid includes engine fuel or engine oil, and the component of interest includes sulfur or a sulfur compound. In certain embodiments, the working engine fluid includes engine oil, and wherein the component of interest comprises one of water and ethylene glycol. In certain embodiments, the working engine fluid includes engine coolant, the component of interest includes a component indicative of engine coolant quality, and the controller is further structured to determine an engine coolant quality index in response to the concentration of the component of interest.

In certain embodiments, the working engine fluid includes engine oil, the component of interest includes a component indicative of engine oil quality, and the controller is further structured to determine an engine oil quality index in response to the concentration of the component of interest. In certain embodiments, the working engine fluid includes a engine oil, engine fuel, engine coolant, an exhaust gas fluid, a recirculating exhaust gas fluid, and/or an engine intake fluid.

In certain embodiments, the system further includes a kit having the first metal tube, the second metal tube, the first window, the second window, and at least a portion of the sample channel, and the kit further includes means for quick removal and replacement.

One exemplary embodiment is an apparatus including an electromagnetic (EM) source control module structured to provide EM radiation signal, an EM source structured to emit EM radiation through a first metal tube and a sample channel in response to the EM radiation signal, wherein the EM radiation comprises energy at a wavelength of interest, and wherein the sample channel contains a working engine fluid. In certain embodiments, the apparatus further includes an EM detector structured to receive the EM radiation from the sample channel through a second metal tube, and further structured to provide a composition indicator signal in response to a remaining radiation strength at the wavelength of interest, and a composition determination module structured to determine a concentration of a component of interest according to the composition indicator signal.

In certain embodiments, the EM source control module is further structured to provide an EM diagnostic signal, where the EM source is further structured to emit an EM diagnostic radiation in response to the EM diagnostic signal, where the EM diagnostic radiation comprises energy at a diagnostic wavelength, where the EM detector is further structured to provide a received diagnostic signal in response to a remaining EM diagnostic radiation strength at the diagnostic wavelength, and the apparatus further includes a diagnostic module structured to determine an amount of soot in response to the received diagnostic signal. In certain embodiments, the composition determination module is further structured to determine the concentration of the component of interest according a corrected composition indicator signal, and to determine the corrected composition indicator signal according to the equation $$CCIS = \frac{Active - Dark}{Inactive - Dark},$$

where CCIS includes corrected composition indicator signal, Active includes the composition indicator signal, Inactive includes the received diagnostic signal, and Dark includes a detected response at a time when the EM source is not emitting a radiation.

In certain embodiments, the diagnostic module is further structured to determine the amount of soot by filtering the received diagnostic signal with a time constant less than 30 seconds to provide an Inactive fast response signal, filtering the received diagnostic signal with a time constant greater than 30 seconds to provide an Inactive slow response signal, and determining the amount of soot according to the Inactive slow response signal subtracted from the Inactive fast response signal. In certain embodiments, the apparatus further includes a first window isolating the first metal tube from the sample channel and a second window isolating the second metal tube from the sample channel, and the diagnostic module is further structured to determine an amount of debris accumulated on at least one of the first window and the second window according to the Inactive slow response signal.

In certain embodiments, the apparatus further includes a first window isolating the first metal tube from the sample channel and a second window isolating the second metal tube from the sample channel, and the diagnostic module is further structured to determine an amount of debris accumulated on at least one of the first window and the second window according to a lowest Inactive observed over time. In certain embodiments, the apparatus further includes a window cleaning module structured to provide a window cleaning index value in response to the amount of debris accumulated. In certain embodiments, the window cleaning module is further structured to provide a window cleaning request signal in response to the window cleaning index value exceeding a cleaning threshold value, and the apparatus further includes a window cleaning means that cleans at least one of the first window and the second window in response to the window cleaning request signal. In certain embodiments, the first metal tube and the second metal tube are the same tube.

One exemplary embodiment is a method including operating an internal combustion engine that includes several combustion chambers each with a dedicated working engine fluid pathway to receive gas for combustion and discharge exhaust. The method includes flowing working engine fluid through the dedicated working engine fluid pathway of one of the chambers during the operating of the engine. The method further includes, as the working engine fluid flows through the pathway, interrogating the working engine fluid with electromagnetic radiation at one or more selected wavelengths, and detecting a response to the radiation. The method further includes generating a signal representative of an amount of a constituent of interest in the working engine fluid. In certain embodiments, the method further includes the working engine fluid pathway including a region from an intake manifold on an upstream side to a turbocharger on a downstream side. In certain embodiments, the method further includes the working engine fluid pathway comprises a region corresponding to a specific cylinder, selected from the regions consisting of an intake port, a combustion chamber, and an exhaust port.

One exemplary embodiment includes a method for operating an internal combustion engine that includes several combustion chambers and an exhaust recirculation subsystem to selectively return exhaust from an exhaust collection point downstream from the combustion chambers to an exhaust return point upstream of the combustion chambers. In certain embodiments, during the operating of the engine, the method includes flowing a working engine fluid through the combustion chambers, interrogating the working engine fluid with electromagnetic radiation at one or more selected wavelengths as the working engine fluid flows along a pathway from the exhaust return point to the exhaust discharge point, and detecting a response to the radiation. In certain embodiments, the method includes generating a signal representative of an amount of a constituent of interest in the working engine fluid.

While the invention has been illustrated and described in detail in the drawings and foregoing description, the same is to be considered as illustrative and not restrictive in character, it being understood that only certain illustrative embodiments have been shown and described and that all changes and modifications that come within the spirit of the inventions are desired to be protected. It should be understood that any relative characterization of embodiments such as but not limited to preferable, preferably, preferred, more preferred, advantageous, or exemplary utilized in the description above indicate that the embodiments or features thereof so described may be more desirable or characteristic, nonetheless the embodiments or features thereof may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A method comprising:
   interrogating a working engine fluid in-situ on the engine with electromagnetic (EM) radiation through a first conduit at a wavelength of interest;
   selecting the wavelength of interest as a wavelength near a responsive wavelength for a constituent of the working engine fluid, but having reduced extinction relative to the responsive wavelength;
   detecting a response of the working engine fluid to the radiation through a second conduit, wherein the first conduit and the second conduit are structured convey the EM radiation to and from the working fluid by internally reflecting the EM radiation through the first conduit and the second conduit; and
   generating a composition indicator signal representative of an amount of the constituent of the working engine fluid in response to the detecting.

2. The method of claim 1, wherein the first conduit and the second conduit each comprise at least one metal selected from the metals consisting of extruded aluminum, extruded stainless steel, a polished metal, and a machined metal.

3. The method of claim 1, wherein the first conduit comprises a first metal tube and wherein the second conduit comprises a second metal tube, and wherein the interrogating the working engine fluid with EM radiation through the first conduit at the wavelength of interest comprises emitting a broad EM radiation and passing the broad EM radiation through a band pass filter.

4. The method of claim 1, wherein the first conduit comprises a first metal tube and wherein the second conduit comprises a second metal tube, and wherein the interrogating the working engine fluid with EM radiation through the first conduit at the wavelength of interest comprises emitting EM radiation at the wavelength of interest from a laser.

5. The method of claim 1, wherein the first conduit comprises a first metal tube and wherein the second conduit comprises a second metal tube, isolating the first metal tube from the working engine fluid with a first window and isolating the second metal tube from the working engine fluid with a second window, and wherein the constituent of the working engine fluid comprises carbon dioxide, and, wherein the first window and the second window comprise sapphire.

6. The method of claim 1, wherein the first conduit comprises a first metal tube and wherein the second conduit comprises a second metal tube.

7. The method of claim 1, further comprising selecting the wavelength of interest such that an extinction of the wavelength of interest is about 50% of an extinction of the responsive wavelength.

8. The method of claim 1, wherein the responsive wavelength comprises one of a fundamental wavelength and a harmonic wavelength.

9. The method of claim 1, further comprising interrogating the working engine fluid with EM radiation through the first conduit at a second wavelength of interest, detecting a second response of the working engine fluid to the radiation through a second conduit, and generating a second composition indicator signal representative of an amount of a second constituent of the working engine fluid.

10. The method of claim 1, wherein the first conduit comprises a first metal tube and wherein the second conduit comprises a second metal tube, the method further comprising isolating the first metal tube from the working engine fluid with a first window and isolating the second metal tube from the working engine fluid with a second window, determining a path length from the first window to the second window, determining a plurality of extinction rates corresponding to a plurality of responsive frequencies for the constituent of the working engine fluid at a design range of concentrations, and selecting the wavelength of interest according to the extinction rates and the path length.

11. The method of claim 1, wherein the first conduit comprises a first metal tube and wherein the second conduit comprises a second metal tube, the method further comprising isolating the first metal tube from the working engine fluid with a first window and isolating the second metal tube from the working engine fluid with a second window;
   providing a replacement kit comprising the first metal tube, the second metal tube, the first window, and the second window;
   removing a previously installed kit from an engine; and
   installing the replacement kit on the engine.

12. The method of claim 1, further comprising interrogating the working engine fluid with EM radiation through the first conduit at a diagnostic wavelength, detecting a diagnostic response of the working engine fluid to the radiation through the second conduit, and generating a diagnostic signal in response to the diagnostic response.

13. The method of claim 12, further comprising determining a fault value in response to the diagnostic signal.

14. A system, comprising:
   an engine having a sample channel comprising a conduit for a working engine fluid;
   an electromagnetic (EM) source structured to emit EM radiation through a first conduit comprising a metal tube, the EM radiation comprising EM energy at a wavelength of interest, wherein the wavelength of interest is a wavelength near a responsive wavelength for a component of interest of the working engine fluid, but having reduced extinction relative to the responsive wavelength;
   an EM detector structured to receive a remainder radiation through a second conduit comprising a metal tube, the remainder radiation comprising the remaining EM radiation after passing through the sample channel, wherein the first conduit and the second conduit are structured convey the EM radiation to and from the sample channel by internally reflecting the EM radiation through the first conduit and the second conduit;

a controller structured to:

determine a composition indicator signal representative of an amount of a component of interest in the working engine fluid in response to a strength of the remainder radiation; and determine a concentration of the component of interest according to the composition indicator signal.

15. The system of claim 14, wherein the EM source comprises at least one of a laser device, a light emitting diode, and a gallium arsenide light emitting diode.

16. The system of claim 14, wherein the EM detector comprises a lead selenide detection device.

17. The system of claim 14, further comprising an interference filter disposed between the EM source and the sample channel, the interference filter comprising a band pass filter.

18. The system of claim 14, further comprising a first window isolating the first conduit from the sample channel, a second window isolating the second conduit from the sample channel, and wherein the first window and the second window comprise a material selected from the group consisting of sapphire, glass, and diamond.

19. The system of claim 18, wherein the working engine fluid comprises a fluid selected from the fluids consisting of engine exhaust gas, recirculating exhaust gas, engine intake gas, engine intake gas corresponding to a single cylinder of a multi-cylinder engine, and engine exhaust gas corresponding to a single cylinder of a multi-cylinder engine.

20. The system of claim 14, wherein the component of interest comprises a component selected from the group consisting of a nitrogen-oxygen compound, a hydrocarbon, a sulfur containing compound, ammonia, a compound representative of a natural gas content, a carbon-oxygen compound, and an amount of particulates.

21. The system of claim 14, wherein the component of interest comprises a component selected from the group consisting of methane, ethane, and propane.

22. The system of claim 14, wherein the component of interest comprises a component selected from the group consisting of nitrogen oxide ($N_yO_x$), nitric oxide (NO), nitrogen dioxide ($NO_2$), and nitrous oxide ($N_2O$).

23. The system of claim 14, wherein the component of interest comprises a component selected from the group consisting of carbonyl sulfide (O=C=S), carbon monoxide, and carbon dioxide.

24. The system of claim 14, wherein the component of interest comprises a component indicative of engine wear, and wherein the controller is further structured to determine an engine wear index in response to the concentration of the component of interest.

25. The system of claim 14, wherein the component of interest comprises a component indicative of fuel quality, and wherein the controller is further structured to determine a fuel quality index in response to the concentration of the component of interest.

26. The system of claim 14, wherein the working engine fluid comprises one of engine fuel and engine oil, and wherein the component of interest comprises one of sulfur and a sulfur compound.

27. The system of claim 14, wherein the working engine fluid comprises engine oil, and wherein the component of interest comprises one of water and ethylene glycol.

28. The system of claim 14, wherein the working engine fluid comprises engine coolant, wherein the component of interest comprises a component indicative of engine coolant quality, and wherein the controller is further structured to determine an engine coolant quality index in response to the concentration of the component of interest.

29. The system of claim 14, wherein the working engine fluid comprises engine oil, wherein the component of interest comprises a component indicative of engine oil quality, and wherein the controller is further structured to determine an engine oil quality index in response to the concentration of the component of interest.

30. The system of claim 14, wherein the working engine fluid comprises a fluid selected from the fluids consisting of engine oil, engine fuel, engine coolant, an exhaust gas fluid, a recirculating exhaust gas fluid, and an engine intake fluid.

31. The system of claim 18, further comprising a kit including the first metal tube, the second metal tube, the first window, the second window, and at least a portion of the sample channel, the kit further including means for quick removal and replacement.

32. An apparatus, comprising:

an electromagnetic (EM) source control module structured to provide an EM radiation signal;

an EM source structured to emit EM radiation through a first conduit comprising a sample channel in response to the EM radiation signal, wherein the EM radiation comprises energy at a wavelength of interest, and wherein the sample channel contains a working engine fluid, wherein the wavelength of interest is a wavelength near a responsive wavelength for a component of interest of the working engine fluid, but having reduced extinction relative to the responsive wavelength;

an EM detector structured to receive the EM radiation from the sample channel through a second conduit, and further structured to provide a composition indicator signal in response to a remaining radiation strength at the wavelength of interest, wherein the first conduit and the second conduit are structured convey the EM radiation to and from the sample channel by internally reflecting the EM radiation through the first conduit and the second conduit; and a composition determination module structured to determine a concentration of the component of interest in response to the composition indicator signal.

33. The apparatus of claim 32, wherein the EM source control module is further structured to provide an EM diagnostic signal, wherein the EM source is further structured to emit EM diagnostic radiation in response to the EM diagnostic signal, wherein the EM diagnostic radiation comprises energy at a diagnostic wavelength, wherein the EM detector is further structured to provide a diagnostic signal in response to a remaining EM diagnostic radiation strength at the diagnostic wavelength, the apparatus further comprising a diagnostic module structured to determine an amount of soot in response to the diagnostic signal.

34. The apparatus of claim 32, wherein the first conduit and the second conduit comprise the same tube.

* * * * *